US009186599B2

(12) United States Patent
Guixa Guardia et al.

(10) Patent No.: US 9,186,599 B2
(45) Date of Patent: Nov. 17, 2015

(54) PROCESS FOR ISOLATING TETRAHYDROFURAN

(75) Inventors: Maria Guixa Guardia, Mannheim (DE); Rolf Pinkos, Bad Duerkheim (DE); Nadja Pollmer, Bissersheim (DE); Wolf-Steffen Weissker, Lambsheim (DE); Hugues Vandenmersch, Jardine's Lookout (HK)

(73) Assignee: BASF SE, Ludwigshafen (DE)

( * ) Notice: Subject to any disclaimer, the term of this patent is extended or adjusted under 35 U.S.C. 154(b) by 918 days.

(21) Appl. No.: 13/235,427

(22) Filed: Sep. 18, 2011

(65) Prior Publication Data

US 2012/0073953 A1 Mar. 29, 2012

Related U.S. Application Data

(60) Provisional application No. 61/385,978, filed on Sep. 24, 2010.

(51) Int. Cl.
| | | |
|---|---|---|
| *C07D 307/00* | (2006.01) | |
| *B01D 3/14* | (2006.01) | |
| *B01D 3/36* | (2006.01) | |
| *C07D 307/36* | (2006.01) | |

(52) U.S. Cl.
CPC ....... *B01D 3/143* (2013.01); *B01D 3/36* (2013.01); *C07D 307/36* (2013.01)

(58) Field of Classification Search
CPC .................................................... C07D 307/08
USPC ......................................................... 549/429
See application file for complete search history.

(56) References Cited

U.S. PATENT DOCUMENTS

| | | | |
|---|---|---|---|
| 4,751,334 A | 6/1988 | Turner et al. | |
| 4,795,824 A | 1/1989 | Kippax et al. | |
| 5,310,954 A | 5/1994 | Hiles et al. | |

FOREIGN PATENT DOCUMENTS

| | | |
|---|---|---|
| DE | 29 27 931 A1 | 1/1981 |
| EP | 0 062 874 A1 | 10/1982 |
| EP | 0 255 399 A2 | 2/1988 |
| GB | 1 402 507 | 8/1975 |

(Continued)

OTHER PUBLICATIONS

International Search Report issued Dec. 7, 2011 in Patent Application No. PCT/EP2011/065314.

*Primary Examiner* — Andrew D Kosar
*Assistant Examiner* — Raymond Covington
(74) *Attorney, Agent, or Firm* — Oblon, McClelland, Maier & Neustadt, L.L.P.

(57) ABSTRACT

A process which isolates tetrahydrofuran from a stream of tetrahydrofuran, alkanol and high boilers, by: (a) separating off a first stream of tetrahydrofuran and alkanol as azeotrope in a first distillation stage; (b) feeding part of the first stream into a reactor for esterifying maleic anhydride, giving a second stream of tetrahydrofuran and monoalkyl maleate; (c) separating the second stream into a third stream of monoalkyl maleate and a fourth stream of tetrahydrofuran in a second distillation stage; (d) feeding the fourth stream of tetrahydrofuran from the second distillation stage and the part of the first stream from (a) which is not fed to the reactor into a third distillation stage to obtain a product stream of tetrahydrofuran and a sixth stream of tetrahydrofuran and alkanol; (e) recirculating the sixth stream from the third distillation stage into the first distillation stage or the reactor in (b).

9 Claims, 2 Drawing Sheets

(56) References Cited

FOREIGN PATENT DOCUMENTS

| | | |
|---|---|---|
| WO | WO 88/00937 A1 | 2/1988 |
| WO | WO 90/03127 A1 | 4/1990 |
| WO | WO 91/01960 A1 | 2/1991 |
| WO | WO 97/43242 A1 | 11/1997 |
| WO | WO 99/48852 A1 | 9/1999 |
| WO | WO 03/006446 A1 | 1/2003 |
| WO | WO 2005/058855 A1 | 6/2005 |

PROCESS FOR ISOLATING TETRAHYDROFURAN

CROSS REFERENCE TO RELATED APPLICATION

This application claims the benefit of U.S. provisional application No. 61/385,978, filed on Sep. 24, 2010.

The invention proceeds from a process for isolating tetrahydrofuran from a stream comprising tetrahydrofuran, alkanol and high boilers, in which a stream comprising tetrahydrofuran and alkanol as azeotrope is separated off in a first distillation step and tetrahydrofuran is isolated as product from the azeotrope in a further distillation step.

Tetrahydrofuran is generally prepared in the preparation of 1,4-butanediol and γ-butyrolactone. In the preparation, maleic anhydride obtained, for example, from butane or benzene by oxidation is generally esterified by means of an alkanol to form monoalkyl maleate in a first stage. The esterification of the maleic anhydride with the alkanol is usually carried out in the absence of catalysts. In a second esterification, the monoalkyl maleate is reacted with alkanol to form dialkyl maleate. The conversion of the monoalkyl maleate into dialkyl maleate is usually carried out in the presence of a catalyst and is carried out in a reaction column. Apart from a two-stage reaction, a single-stage conversion of maleic anhydride into dialkyl maleate is also possible.

The dialkyl maleate is, depending on the catalyst system used, hydrogenated in a further step to form a mixture of 1,4-butanediol, tetrahydrofuran and γ-butyrolactone, a mixture of tetrahydrofuran and γ-butyrolactone or tetrahydrofuran. A corresponding process for preparing 1,4-butanediol, γ-butyrolactone and tetrahydrofuran is defined, for example, in WO 99/48852. Corresponding processes for preparing 1,4-butanediol, γ-butyrolactone and tetrahydrofuran are also known from EP-A 0 255 399, WO 97/43242 and U.S. Pat. No. 4,751,334.

To isolate the individual reaction products, the mixture comprising 1,4-butanediol, γ-butyrolactone and tetrahydrofuran is distilled in a first column. In this, a mixture comprising alkanol and tetrahydrofuran as azeotrope is taken off at the top. To isolate the tetrahydrofuran, this mixture is fed to a second distillation column in which tetrahydrofuran is taken off as high boiler and a mixture comprising tetrahydrofuran and alkanol is taken off at the top and recirculated to the first distillation column. Alkanol, 1,4-butanediol and γ-butyrolactone are taken off at the bottom of the first distillation column and passed to further processing. The work-up of the product mixture comprising 1,4-butanediol, γ-butyrolactone and tetrahydrofuran is described, for example, in DE-C 29 27 931 or U.S. Pat. No. 5,310,954.

The overall process for preparing 1,4-butanediol, in which tetrahydrofuran is also formed, and the work-up of the product mixture is known, for example, from WO-A 91/01960.

A disadvantage of the process described is in each case that a relatively large proportion of tetrahydrofuran is separated off together with the alkanol at the top of the second distillation column, so that a large proportion of product is recirculated to the first distillation column.

It is therefore an object of the present invention to provide a process for isolating tetrahydrofuran from a stream comprising tetrahydrofuran and alkanol as azeotrope, in which the stream comprising methanol and tetrahydrofuran which is to be recirculated is minimized and the capacity for tetrahydrofuran of the distillation sequence can thus be increased.

The object is achieved by a process for isolating tetrahydrofuran from a stream comprising tetrahydrofuran, alkanol and high boilers, which comprises the following steps:

(a) separating off a stream comprising tetrahydrofuran and alkanol as azeotrope in a first distillation stage, (b) feeding at least part of the stream comprising tetrahydrofuran and alkanol as azeotrope into a reactor for esterifying maleic anhydride, giving a stream comprising tetrahydrofuran, optionally alkanol, optionally unreacted maleic anhydride and monoalkyl maleate, (c) separating the stream comprising monoalkyl maleate, tetrahydrofuran and optionally alkanol into a stream comprising monoalkyl maleate and a stream comprising tetrahydrofuran and optionally alkanol in a second distillation stage, (d) feeding the stream comprising tetrahydrofuran and optionally alkanol from the second distillation stage and the part of the stream comprising tetrahydrofuran and alkanol as azeotrope from step (a) which is not fed to the reactor into a third distillation stage in which a product stream comprising essentially tetrahydrofuran and a stream comprising tetrahydrofuran and alkanol are obtained, (e) recirculating the stream comprising tetrahydrofuran and alkanol from the third distillation stage to the first distillation stage or to the reactor in step (b).

As a result of at least part of the stream comprising tetrahydrofuran and alkanol as azeotrope being fed into a reactor for esterifying maleic anhydride, in which a stream comprising tetrahydrofuran, alkanol and monoalkyl maleate is obtained, and separating the stream into a stream comprising monoalkyl maleate and a stream comprising tetrahydrofuran and alkanol, at least part of the alkanol comprised in the stream comprising tetrahydrofuran and alkanol as azeotrope is consumed in the reaction, so that a greater proportion of tetrahydrofuran is obtained together with any remaining alkanol at the third distillation step. The proportion of tetrahydrofuran obtained as product is increased in this way. No alkanol is comprised in the stream obtained in the reaction in step (b) if the alkanol is completely reacted in the reaction step. However, full conversion is usually not obtained, so that alkanol is comprised in the stream.

For the purposes of the present invention, "comprising essentially tetrahydrofuran" means that at least 98% by weight, preferably at least 98.5% by weight, of tetrahydrofuran is comprised in the stream The stream comprising tetrahydrofuran, alkanol and high boilers usually originates from a hydrogenation in which dialkyl maleate is hydrogenated. Apart from tetrahydrofuran and alkanol, the stream can generally comprise 1,4-butanediol and/or γ-butyrolactone. Depending on the catalyst system used, the stream comprises tetrahydrofuran, 1,4-butanediol and γ-butyrolactone; tetrahydrofuran and γ-butyrolactone; tetrahydrofuran and 1,4-butanediol or only tetrahydrofuran. These are separated off as high boilers in the first distillation stage. Apart from the desired materials tetrahydrofuran, γ-butyrolactone and 1,4-butanediol, the alkanol formed and in general also water are comprised in the stream. The water and alkanol are likewise separated off as high boilers in the first distillation step. In general, the stream comprising tetrahydrofuran, alkanol and high boilers comprises from 2 to 30% by weight of tetrahydrofuran, from 0 to 20% by weight of γ-butyrolactone, from 20 to 50% by weight of 1,4-butanediol, from 30 to 50% by weight of alkanol, from 0 to 8% by weight of water, from 0 to 2% by weight of butanol and from 0 to 5% by weight of dimethyl succinate. The stream comprising tetrahydrofuran, alkanol and high boilers preferably comprises from 5 to 15% by weight of tetrahydrofuran, from 5 to 15% by weight of γ-butyrolactone, from 30 to 45% by weight of 1,4-butanediol, from 35 to 45% by weight of alkanol, from 1 to 5% by weight of water, from 0.2 to 1.5% by weight of butanol and from 0 to 1.5% by weight of dimethyl succinate.

In the process for preparing tetrahydrofuran, maleic anhydride is generally reacted with alkanol to form monoalkyl maleate in an equilibrium reaction in a first esterification reactor. The monoalkyl maleate is reacted with alkanol to form dialkyl maleate in a second esterification reactor and the dialkyl maleate is subsequently hydrogenated to tetrahydrofuran and optionally 1,4-butanediol and/or γ-butyrolactone.

The alkanol used for preparing tetrahydrofuran from maleic anhydride is generally a $C_1$-$C_4$-alkanol. Suitable $C_1$-$C_4$-alkanols comprise, in particular, methanol, ethanol, n-propanol, isopropanol and butanol. Methanol and ethanol, in particular methanol, are preferably used as alkanols.

The reaction of the maleic anhydride with alkanol to form monoalkyl maleate in the first esterification reactor is usually carried out in the absence of catalysts. Conversion of the monoalkyl maleate into the corresponding dialkyl maleate can occur as early as in this reaction.

The first esterification reactor in which an uncatalyzed reaction of the maleic anhydride takes place is usually operated at a temperature in the range from 65° C. to 260° C. and a pressure in the range from 1 to 50 bar. The first esterification reactor is usually followed by a second esterification reactor in which a catalytic esterification is carried out. The second esterification stage can comprise a plurality of stirred tank reactors, as described, for example, in U.S. Pat. No. 4,795,824. However, the catalytic esterification stage preferably comprises a reactive column as is described, for example, in WO-A 90/03127. In this case, the first esterification stage can comprise a stirred tank or a reactive column having one or more trays as reactor, with no esterification catalyst being comprised. The reactive column is supplied at the bottom with alkanol vapor, while the maleic anhydride solution is passed in countercurrent through the reactive column.

When the second esterification stage which is operated catalytically comprises a reactive column, the solution comprising monoalkyl maleate is fed in at the uppermost tray of the reactive column, while an excess of alkanol vapor is introduced at the bottom of the reactive column.

In the catalytically operated second esterification stage, each tray of the reactive column comprises a charge of esterification catalyst.

A possible alternative to a tray column as reactive column is, for example, to use a packed column as reactive column, with the packing comprising the catalyst.

When a tray column is used, it is possible to use any trays, for example sieve trays or bubble cap trays.

Typical reaction conditions under which the reactive column is operated comprise a temperature and a pressure under which the alkanol used distills. These temperature and pressure conditions vary as a function of the alkanol selected. The temperatures are usually in the range from 65 to 135° C. and the pressure is usually in the range from 1 to 3 bar. As esterification catalyst, it is possible to use, for example, an ion-exchange resin marketed under the trade name Amberlyst™ by Rohm & Haas.

Acids present in the maleic anhydride, for example acetic acid or acrylic acid, are reacted together with maleic acid or fumaric acid which is present in the solution fed to the first esterification stage to form the corresponding $C_1$-$C_4$-alkyl ester or diester.

A stream comprising $C_1$-$C_4$-alkanol vapor and water vapor is taken off at the top of the reactive column. Furthermore, traces of minor by-products such as dialkyl ether, traces of the dialkyl maleate and of the alkyl acrylate can be comprised. To recirculate the dialkyl maleate, additional trays which act as a scrubbing column in which the dialkyl maleate is scrubbed out can be provided above the uppermost esterification tray. In general, the stream taken off at the top of the reactive column comprises from 30 to 90% by weight of alkanol, from 10 to 50% by weight of water and traces of minor secondary components.

In this case, a vapor stream which is essentially free of dialkyl maleate leaves the top of the reactive column.

A liquid stream comprising a solution of the dialkyl maleate is obtained at the bottom of the reactive column. In general, the stream obtained at the bottom of the reactive column comprises more than 80% by weight of the dialkyl maleate, less than 20% of alkanol and traces of minor secondary components.

Apart from the above-described two-stage esterification, the esterification of the stream comprising maleic anhydride can also be carried out in one stage. This single-stage procedure is described, for example, in EP-A 0 062 874. In one suitable embodiment, for example, the maleic anhydride-comprising stream and the alkanol are fed in together with a catalyst which is generally acidic (e.g. sulfuric acid or an acid ion exchanger) at the top of a suitable tray column serving as reaction column. Water formed in the esterification is taken off in the form of aqueous alcohol at the top of the column, and the aqueous alcohol taken off is dewatered in a separate plant. The alkanol is optionally recirculated to the column. A dialkyl maleate-comprising stream is taken off at the bottom of the reaction column.

The dialkyl maleate-comprising stream which is obtained in the second esterification stage or in the single-stage process is fed to a hydrogenation. The hydrogenation is advantageously carried out in the vapor phase using a heterogeneous ester hydrogenation catalyst. Suitable ester hydrogenation catalysts are, for example, reduced copper catalysts with promoter, for example reduced copper chromite catalysts.

The catalyst particles preferably have a particle size in the range from 0.5 to 5 mm. The particles can have any suitable shape, for example spheres, pellets, rings or saddles. When a fixed catalyst bed is used, the reactor can be a shell-and-tube reactor which can operate essentially isothermally. However, preference is given to an adiabatic reactor.

The hydrogenation is generally carried out at an elevated temperature in the range from 150 to 240° C. and a pressure in the range from 5 to 100 bar, preferably from 50 to 70 bar. Such a hydrogenation is described, for example, in WO-A 88/00937; WO-A 91/01960, U.S. Pat. No. 4,751,334, WO-A 03/006446 or WO-A 05/058855.

The hydrogenation gives a product mixture which comprises the $C_1$-$C_4$-alkanol used together with tetrahydrofuran and optionally 1,4-butanediol and/or γ-butyrolactone. This stream additionally comprises, inter alia, n-butanol, dimethyl succinate and water. This product mixture is fed as stream comprising tetrahydrofuran, alkanol and high boilers to the process for isolating tetrahydrofuran in step (a).

In a first embodiment of the invention, the reactor for esterifying maleic anhydride, into which part of the stream comprising tetrahydrofuran and alkanol as azeotrope is fed, is the reactor of the first esterification stage of the process for preparing tetrahydrofuran from which the stream comprising tetrahydrofuran, alkanol and high boilers originates.

It has surprisingly been found that the tetrahydrofuran which is introduced together with the alkanol into the first esterification stage has no adverse effects on the first esterification stage.

After the first esterification stage has been carried out, the stream comprising monoalkyl maleate obtained in the esterification stage, which also comprises the unreacted tetrahydrofuran, is fed to the distillation in step (c). Here, the monoalkyl maleate is separated off as high boiler from the stream comprising tetrahydrofuran and residual alkanol. The monoalkyl maleate is fed to the second esterification stage and the low boiler stream which is separated off at the top and comprises tetrahydrofuran and alkanol is fed to the third distillation stage in step (d) to separate off the tetrahydrofuran.

In an alternative embodiment, the reactor for esterifying maleic anhydride in step (b) and the reactor of the first esterification stage are two separate reactors. The reactor used for esterifying maleic anhydride in step (b) can correspond in terms of construction to the reactor of the first esterification stage. Furthermore, the process conditions under which the maleic anhydride is esterified in the reactor are the same as those in the first esterification stage of the main process. For the present purposes, the main process is the process for preparing tetrahydrofuran, 1,4-butanediol and γ-butyrolactone from which the stream comprising tetrahydrofuran, alkanol and high boilers which is distilled in the first distillation step (a) originates.

When a separate reactor is used for esterifying maleic anhydride in step (b), maleic anhydride is introduced into this reactor in such an amount that the molar ratio of acid anhydride to alcohol is in the range from 1:10 to 10:1, preferably from 5:1 to 1:5 and particularly preferably from 3:1 to 1:3. The reactor can be operated continuously or batchwise. Suitable reactors are, for example, tube reactors or stirred tank reactors. The reaction of the first esterification stage in which the alkanol is reacted with maleic anhydride to form monoalkyl maleate is preferably carried out in the range from 50 to 150° C., in particular from 60 to 130° C., at a pressure at which the alcohol remains in the liquid phase, for example in the range from 1 to 20 bar. The residence time is preferably selected in the range from 5 to 300 minutes, more preferably 5-120 minutes, for example 60 minutes. The residence time is preferably set so that the methanol conversion is in the range from 30 to 100%, in particular from 40 to 85%. Apart from the monoalkyl maleate, tetrahydrofuran and alkanol, the mixture obtained in the first esterification stage can additionally comprise dialkyl maleate, unreacted maleic anhydride and water.

The stream comprising tetrahydrofuran, optionally alkanol and monoalkyl maleate leaving the esterification reactor is fed to the second distillation stage (c). In this, tetrahydrofuran and alkanol are separated from the monoalkyl maleate. The second distillation stage is operated so that the stream comprising essentially tetrahydrofuran which is separated off in the third distillation stage (d) has the prescribed purity. This means that the stream fed to the third distillation stage (d) no longer comprises any high boilers such as monoalkyl maleate, dialkyl maleate and maleic anhydride.

The stream comprising monoalkyl maleate which is obtained in the second distillation stage (c) can comprise maleic anhydride, tetrahydrofuran and alkanol in addition to the monoalkyl maleate. This monoalkyl maleate-comprising stream is processed further.

For this purpose, particular preference is given to feeding the monoalkyl maleate into the first or second esterification stage of the main process in which it is converted into dialkyl maleate. In general, the monoalkyl maleate-comprising stream comprises from 50 to 95% by weight of monoalkyl maleate, from 1 to 50% by weight of maleic anhydride, from 0 to 5% by weight of dialkyl maleate, from 0 to 5% by weight of tetrahydrofuran, from 0 to 3% by weight of water and traces of minor secondary components.

The first distillation step (a) in which tetrahydrofuran and alkanol are separated off as azeotrope from the stream comprising tetrahydrofuran, alkanol and high boilers is generally carried out in a first distillation column. The first distillation column is operated at a pressure in the range from 0.1 to 5 bar, preferably not more than 2 bar, for example 1.1 bar. As distillation column, use is made of a column of any construction type. Suitable columns are, for example, bubble cap tray columns, valve tray columns or columns packed with random packing elements. A column comprising ordered packing can also be used.

The distillation column preferably has from 20 to 60 theoretical plates and reflux ratios in the range from 0.5 to 5. The high boilers, in particular 1,4-butanediol and γ-butyrolactone, and also water and alkanol are taken off at the bottom of the distillation column. The stream comprising tetrahydrofuran and alkanol as azeotrope is taken off at the top of the column.

The composition of the stream comprising tetrahydrofuran and alkanol as azeotrope depends on the alkanol used and the pressure at which the stream is taken off. When the stream comprises alkanol, tetrahydrofuran and alkanol are usually present as azeotrope. Thus, for example, tetrahydrofuran and methanol form an azeotrope at a pressure of 1.2 bar and a ratio of tetrahydrofuran to methanol of 0.67:0.33. At a pressure of 1.4 bar, the ratio of tetrahydrofuran to methanol is 0.65:0.35. Tetrahydrofuran and ethanol form an azeotrope comprising 92.5% by weight of tetrahydrofuran and 7.5% by weight of ethanol at a pressure of 1.1 bar and an azeotrope comprising 88.9% by weight of tetrahydrofuran and 11.1% by weight of ethanol at a pressure of 1.5 bar.

The second distillation stage in which remaining alkanol and tetrahydrofuran are separated from the monoalkyl maleate can likewise be carried out in any suitable distillation apparatus. Here too, a distillation column is particularly suitable. As an alternative, tetrahydrofuran and alkanol can also be separated from the monoalkyl maleate in, for example, a suitable evaporator, for example a falling film evaporator or thin film evaporator. However, preference is given to a distillation column. Here too, the distillation column is preferably a column of any construction type, for example a bubble cap tray column, a valve tray column, a column packed with random packing elements or a column having ordered packing. The column preferably has from 1 to 30 theoretical plates and a reflux ratio in the range from 0.1 to 5.

The pressure at which the second distillation stage is carried out is preferably in the range from 0.1 to 1.2 bar and is usually less than the pressure in the first distillation step.

The stream comprising optionally alkanol and tetrahydrofuran separated off from the stream comprising monoalkyl maleate, tetrahydrofuran and optionally alkanol in the second distillation stage is fed together with the stream comprising tetrahydrofuran and alkanol as azeotrope which has not been fed to the reactor to a third distillation stage. The third distillation stage (step (d)) is preferably likewise carried out in a distillation column. Here too, a column of any construction type, for example a bubble cap tray column, a valve tray column, a column packed with random packing elements or a column having ordered packing can be used. The distillation column of the third distillation stage preferably has from 15 to 50 theoretical plates and is operated at a higher pressure than the column of the first distillation stage, preferably at a pressure in the range from 3 to 25 bar, preferably from 6 to 10 bar.

A stream comprising tetrahydrofuran and alkanol is obtained at the top of the distillation column of the third distillation stage and is recirculated to the first distillation stage (a). The product stream comprising essentially tetrahydrofuran is taken off at the bottom of the distillation column in the third distillation stage.

The proportion of the stream comprising tetrahydrofuran and alkanol as azeotrope which is fed to the reactor for esterifying maleic anhydride in step (b) is preferably in the range from 20 to 100% by weight. The proportion is more preferably in the range from 30 to 80% by weight, for example 50% by weight.

Embodiments of the invention are shown in the figures and are described in more detail in the following description.

Figure 1:
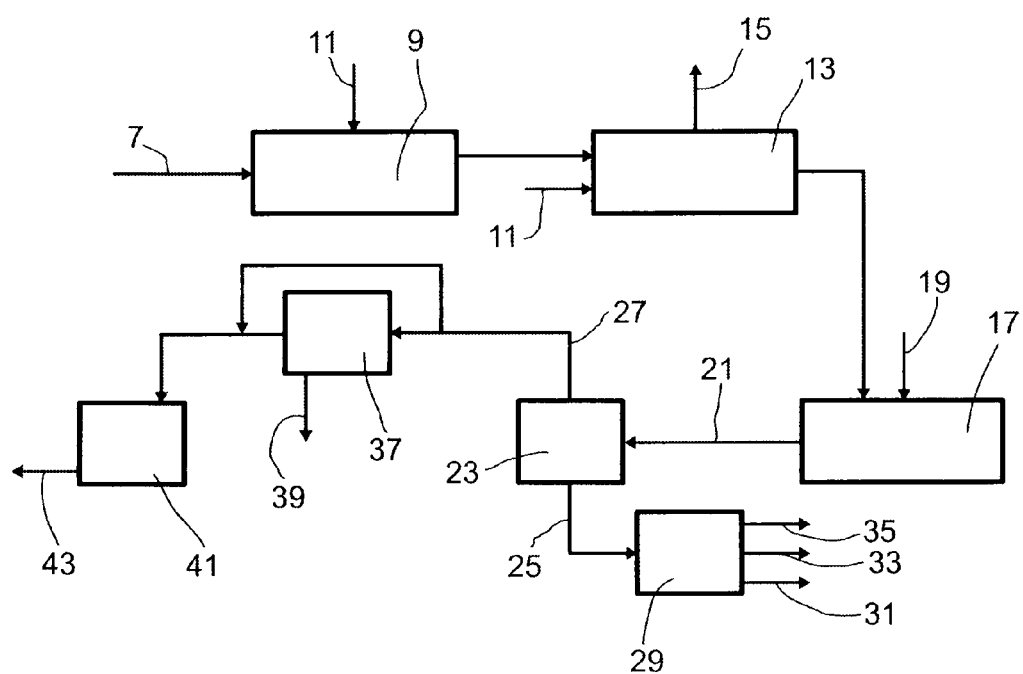
FIG. 1 shows a schematic depiction of the process of the invention.

FIG. 1 schematically shows the process of the invention.

Maleic anhydride is fed via a line 7 to a first esterification stage 9. Apart from the maleic anhydride 7, a $C_1$-$C_4$-alkanol 11 is also fed to the first esterification stage 9. In the first esterification stage 9, the maleic anhydride is reacted with the $C_1$-$C_4$-alkanol to form a monoalkyl maleate.

The $C_1$-$C_4$-alkanol fed is preferably methanol or ethanol, so that the monoalkyl maleate produced in the first esterification stage 9 is monomethyl maleate or monoethyl maleate.

The monoalkyl maleate produced in the first esterification stage 9 is fed together with the unreacted maleic anhydride and unreacted $C_1$-$C_4$-alkanol to a second esterification stage 13. Apart from the stream comprising monoalkyl maleate from the first esterification stage 9, further $C_1$-$C_4$-alkanol 11 is fed to the second esterification stage 13. In the second esterification stage 13, the monoalkyl maleate is reacted with the additional $C_1$-$C_4$-alkanol to form dialkyl maleate. The $C_1$-$C_4$-alkanol fed to the second esterification stage 13 is usually the same $C_1$-$C_4$-alkanol which is fed to the first esterification stage 9. Thus, when methanol is fed to the first esterification stage 9, methanol is also fed to the second esterification stage 13.

Water formed in the esterification in the second esterification stage 13 and also unreacted $C_1$-$C_4$-alkanol are taken off via an outlet 15.

The dialkyl maleate produced in the second esterification stage 13 is fed to a hydrogenation stage 17. For the hydrogenation, hydrogen 19 is also introduced into the hydrogenation stage 17. In the hydrogenation stage 17, the dimethyl maleate is reacted with the hydrogen to form tetrahydrofuran and optionally 1,4-butanediol and/or γ-butyrolactone with simultaneous formation of alkanol and water, as described, for example, in WO 88/00937, WO 91/01960, WO 03/006446 or WO 05/058855. The alkanol formed in the hydrogenation is the same alkanol as that which was introduced in the first esterification stage 9 and second esterification stage 13.

The crude product stream 21 comprising 1,4-butanediol, tetrahydrofuran, γ-butyrolactone, alkanol and water which is produced in the hydrogenation stage is fed to a first distillation stage 23. In the first distillation stage 23, the crude product stream 21, the stream comprising tetrahydrofuran and alkanol and also high boilers, is separated into a bottom stream 25 comprising high boilers and an overhead stream 27 comprising tetrahydrofuran and alkanol as azeotrope. The high boiler-comprising bottom stream 25, which comprises 1,4-butanediol, γ-butyrolactone, alkanol and water, is fed to a high boiler work-up 29 in which this stream is separated into γ-butyrolactone 31, 1,4-butanediol 33 and alkanol and water 35.

The overhead stream 27 comprising tetrahydrofuran and alkanol as azeotrope which is taken off from the first distillation stage 33 is completely or partly fed to an esterification stage 31 into which maleic anhydride is also introduced. In the esterification stage 37, the maleic anhydride is reacted with the alkanol comprised in the overhead stream 27 to form monoalkyl maleate 39. The monoalkyl maleate 39 is preferably introduced into the first esterification stage 11 or the second esterification stage 13. To separate off the monoalkyl maleate 39, the esterification stage 37 comprises a distillation stage in which the monoalkyl maleate is separated from the unreacted alkanol and tetrahydrofuran.

The alkanol which is not reacted in the esterification stage 37 and also the tetrahydrofuran are fed to a third distillation stage 41. Apart from the tetrahydrofuran and alkanol discharged from the esterification stage 37, the part of the stream 27 comprising tetrahydrofuran and alkanol as azeotrope which has not been fed to the esterification stage 37 is also fed to the third distillation stage 41. In the third distillation stage 41, the stream comprising alkanol and tetrahydrofuran is separated into a product stream 43 comprising essentially tetrahydrofuran and a second stream comprising tetrahydrofuran and alkanol, and the stream comprising tetrahydrofuran and alkanol is recirculated to the first distillation stage 23.

Figure 2:
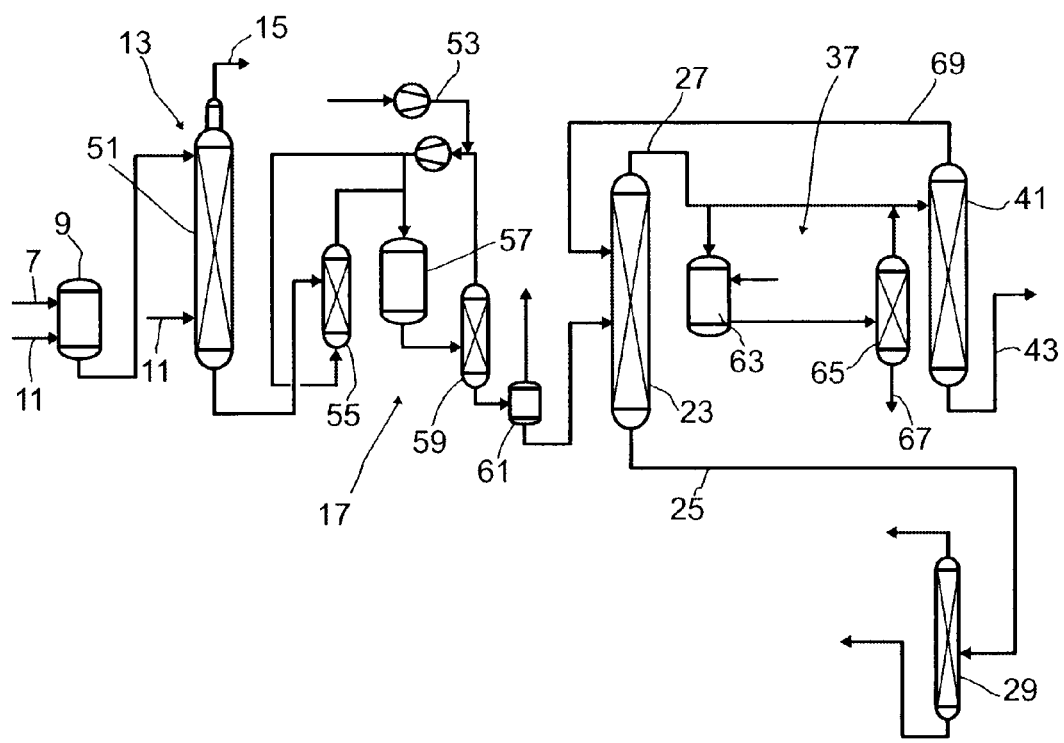
FIG. 2 shows a process flow diagram of the process of the invention.

FIG. 2 shows the process of the invention by way of example as a process flow diagram.

Maleic anhydride is fed via a first feed line 7 to the first esterification stage 9 and the $C_1$-$C_4$-alkanol 11 is fed in via a second feed line. The starting materials can be fed in via separate feed lines as shown in FIG. 2 or else together via one feed line, with in this case the feed line for the $C_1$-$C_4$-alkanol opening into the feed line for the maleic anhydride. A reactor of a construction type known to those skilled in the art, for example a tube reactor or a stirred tank, is used as reactor for the first esterification stage 9. A cascade of reactors is also possible.

The stream comprising monoalkyl maleate, $C_1$-$C_4$-alkanol and unreacted maleic anhydride which was produced in the first esterification stage 9 is fed to the second esterification stage 13. The second esterification stage 13 is, for example, carried out in a reactive column 51. The stream comprising monoalkyl maleate is preferably introduced in the upper region of the reactive column 51 and the $C_1$-$C_4$-alkanol 11 required for the esterification of the monoalkyl maleate to form dialkyl maleate is preferably introduced in the lower region of the reactive column 51. The monoalkyl maleate and the $C_1$-$C_4$-alkanol are thus conveyed in countercurrent in the reactive column 51.

The product stream obtained is at the same time distilled in the reactive column 51, and unreacted $C_1$-$C_4$-alkanol and also water formed in the esterification are taken off at the top. The dialkyl maleate produced in the reactive column 51 is taken off at the bottom of the reactive column 51. This is fed to the hydrogenation stage 17. Hydrogen is fed to the hydrogenation stage 17 via a feed line 53.

The dialkyl maleate is firstly fed to an evaporator 55 through which hydrogen also flows. In the evaporator 55, the dialkyl maleate is vaporized and mixed with the hydrogen. The vaporized dialkyl maleate is fed together with the hydrogen to a hydrogenation reactor 57. In the hydrogenation reactor 57, the dialkyl maleate is converted into 1,4-butanediol, γ-butyrolactone and tetrahydrofuran. The product stream and also by-products and unreacted starting materials are condensed out in a condenser 59 and the unreacted hydrogen is separated off.

The product stream is depressurized in a depressurization vessel 61 and previously dissolved gas which is liberated is separated off.

The crude product stream comprising tetrahydrofuran, alkanol and high boilers is subsequently fed to the first distillation stage 23. High boilers comprised in the crude product stream are 1,4-butanediol, γ-butyrolactone, water and unreacted alkanol.

These are taken off at the bottom of the first distillation stage 23, which is usually configured as a distillation column, and fed to the high boiler work-up 29. In the high boiler work-up 29, alkanol and water are obtained at the top and γ-butyrolactone and 1,4-butanediol are obtained at the bottom. The bottom stream is then separated further into γ-butyrolactone and 1,4-butanediol.

An overhead stream 27 comprising tetrahydrofuran and alkanol as azeotrope is taken off at the top of the distillation column of the first distillation stage 23. Part of this overhead steam 27 comprising tetrahydrofuran and alkanol as azeotrope or the entire overhead stream 27 comprising tetrahydrofuran and alkanol as azeotrope is fed to the esterification stage 37. The first esterification stage 37 comprises an esterification reactor 63 and a second distillation stage 65. In addition to the steam comprising alkanol and tetrahydrofuran as azeotrope, maleic anhydride is also fed to the esterification reactor 63. The maleic anhydride reacts with the alkanol of the stream comprising tetrahydrofuran and alkanol as azeotrope to form monoalkyl maleate. The entire product stream is fed to the second distillation stage 65 in which monoalkyl maleate is taken off as bottom steam 67 and unreacted alkanol and tetrahydrofuran are taken off at the top. The stream comprising tetrahydrofuran and alkanol which is taken off at the top of the second distillation column 65 is introduced together with the part of the overhead stream 27 comprising tetrahydrofuran and alkanol as azeotrope which has not been fed to the esterification reactor 63 into the third distillation stage 41. The third distillation stage 41 is preferably likewise configures as a distillation column. An overhead stream 69 comprising tetrahydrofuran and alkanol is obtained at the top of the third distillation stage 41 and is recirculated to the first distillation stage 63. The product stream 43 comprising essentially tetrahydrofuran is obtained at the bottom of the third distillation stage.

Apart from the embodiment shown in FIG. 2, in which the esterification reactor 63 is an independent reactor, it is also possible to utilize the reactor of the first esterification stage 9. In this case, the part of the overhead stream 27 comprising tetrahydrofuran and alkanol as azeotrope is not fed to a reactor 63 but introduced into the reactor of the first esterification stage 9. When the reactor of the first esterification stage 9 is utilized, the tetrahydrofuran and alkanol are firstly separated off in the second distillation stage 65 after the reactor before the monoalkyl maleate produced in the first esterification stage 9 is fed to the second esterification stage 13.

When a separate reactor 63 is used, as shown in FIG. 2, preference is likewise given to the monoalkyl maleate obtained in the second distillation stage 65 being introduced into the first esterification stage 11 or into the second esterification stage 13.

LIST OF REFERENCE NUMERALS

1 First reactor
3 n-Butane
5 Air
7 Line for maleic anhydride
9 First esterification stage
11 $C_1$-$C_4$-Alkanol
13 Second esterification stage
15 Outlet for $H_2O$/alkanol
17 Hydrogenation stage
19 Hydrogen
21 Crude product
23 First distillation stage
25 Bottom stream comprising high boilers
27 Overhead stream comprising tetrahydrofuran and alkanol
29 High boiler work-up
31 γ-Butyrolactone
33 1,4-Butanediol
35 Alkanol and water
37 Esterification stage
39 Monoalkyl maleate
41 Third distillation stage
43 Tetrahydrofuran-comprising product stream
51 Reactive column
53 $H_2$ feed line
55 Evaporator
57 Hydrogenation reactor
59 Condenser
61 Gas separator
63 Esterification reactor
65 Second distillation stage
67 Bottom stream
69 Overhead stream comprising tetrahydrofuran and alkanol

The invention claimed is:

1. A process for isolating tetrahydrofuran from a stream comprising tetrahydrofuran, alkanol and high boilers, which process comprises:
   (a) separating off a first stream comprising tetrahydrofuran and alkanol as azeotrope from the stream comprising tetrahydrofuran, alkanol and high boilers in a first distillation stage,
   (b) feeding at least part of the first stream comprising tetrahydrofuran and alkanol as azeotrope into a reactor for esterifying maleic anhydride, giving a second stream comprising monoalkyl maleate, tetrahydrofuran, optionally alkanol, and optionally unreacted maleic anhydride,
   (c) separating the second stream comprising monoalkyl maleate, tetrahydrofuran, optionally alkanol, and optionally unreacted maleic anhydride, into a third stream comprising monoalkyl maleate and a fourth stream comprising tetrahydrofuran and optionally alkanol in a second distillation stage,
   (d) feeding the fourth stream comprising tetrahydrofuran and optionally alkanol from the second distillation stage and the part of the stream comprising tetrahydrofuran and alkanol as azeotrope from said (a) separating which is not fed to the reactor into a third distillation stage in which a product stream comprising essentially tetrahydrofuran and a fifth stream comprising tetrahydrofuran and alkanol are obtained,
   (e) recirculating the fifth stream comprising tetrahydrofuran and alkanol from the third distillation stage to the first distillation stage or to the reactor in said (b) feeding.

2. The process according to claim 1, wherein the stream comprising tetrahydrofuran, alkanol and high boilers is obtained by a process for preparing tetrahydrofuran, comprising reacting maleic anhydride with alkanol to form monoalkyl maleate in a first esterification stage, reacting the monoalkyl maleate with alkanol to form a dialkyl maleate in a second esterification stage, and hydrogenating the dialkyl maleate to tetrahydrofuran, 1,4-butanediol and γ-butyrolactone.

3. The process according to claim 1, wherein the high boilers comprise 1,4-butanediol, γ-butyrolactone and water.

4. The process according to claim 2, wherein the reactor for esterifying maleic anhydride in said (b) feeding is the reactor of the first esterification stage.

5. The process according to claim 1, wherein the reactor for esterifying maleic anhydride in said (b) feeding and the reactor of the first esterification stage are two separate reactors.

6. The process according to claim 5, wherein the monoalkyl maleate produced in the reactor for esterifying maleic anhydride in said (b) feeding is fed to the first or second esterification stage.

7. The process according to claim 1, wherein from 20 to 100% by weight of the stream comprising tetrahydrofuran and alkanol as azeotrope is fed to the reactor for esterifying maleic anhydride in said (b) feeding.

8. The process according to claim 1, wherein the alkanol is methanol or ethanol.

9. The process according to claim 1, wherein the reactor for esterifying maleic anhydride in said (b) feeding is operated so that the conversion of alkanol in the reactor is in the range from 30 to 100%.

\* \* \* \* \*